United States Patent [19]
Rohlfing et al.

[11] Patent Number: 5,988,814
[45] Date of Patent: Nov. 23, 1999

[54] PATIENT-INTERACTIVE METHOD AND APPARATUS FOR MEASURING EYE REFRACTION

[75] Inventors: Thomas R. Rohlfing; Bruce E. Erickson, both of Salt Lake City, Utah

[73] Assignee: Evans & Sutherland Computer Corporation, Salt Lake, Utah

[21] Appl. No.: 09/260,348

[22] Filed: Mar. 2, 1999

[51] Int. Cl.⁶ ........................................... A61B 3/10
[52] U.S. Cl. .............................................. 351/212
[58] Field of Search ................................. 351/208, 211, 351/212, 222, 223, 214, 217, 218

[56] References Cited

U.S. PATENT DOCUMENTS

| | | | |
|---|---|---|---|
| 4,730,917 | 3/1988 | Krueger | 351/211 |
| 4,938,584 | 7/1990 | Suematsu et al. | 351/211 |
| 5,011,276 | 4/1991 | Iwamoto | 351/208 |
| 5,016,643 | 5/1991 | Applegate . | |
| 5,360,010 | 11/1994 | Applegate . | |

*Primary Examiner*—George Manuel
*Attorney, Agent, or Firm*—Thorpe, North & Western, LLP

[57] ABSTRACT

A patient-interactive method and apparatus for measuring eye refraction includes a display for producing, alternately, two spaced-apart light spots, and an aperture device for passing light from one spot through an aperture in one position, to travel to the eye, and for passing light from the other spot through an aperture in a second position, to travel to the eye. If the patient sees a single spot, the eye is properly refracting, but if he/she sees two spots, the eye is not properly refracting. Apparatus is provided to allow the patient to adjust the spacing of the light spots, and thus the angle that light enters the eye, until the patient views a single light spot. The amount of adjustment of the spacing of light spots is measured to thereby provide a measure of diopter correction necessary to correct the refraction error.

18 Claims, 5 Drawing Sheets

PATIENT-INTERACTIVE METHOD AND APPARATUS FOR MEASURING EYE REFRACTION

BACKGROUND

1. The Field of the Invention

This invention relates generally to measuring the refractive properties of the eye, and more particularly to a method and apparatus by which a patient may examine and measure the refractive properties of his/her own eyes in a more exact and objective manner than currently available.

2. The Background Art

Measuring the refractive properties of the eye is typically an iterative process, taking a fair amount of time, and involving more than one person, viz., a patient whose eyes are to be examined and an optical technician. The optical technician presents the patient with various calibrated lenses that have different optical properties and through which the patient views a displayed image or test pattern. With each lens, the optical technician asks the patient if vision with the current lens is better than with the immediately prior lens. The patient then attempts to remember and compare the prior image mentally stored in his/her brain with the current image, and make a subjective judgment as to which image is visually better. The comparison of current and prior images (viewed through current and prior calibrated lenses) continues until the patient decides that he/she has viewed the "best" image.

This decision, however, is made without any direct comparison of images. As a result, the patient oftentimes has difficulty being very conclusive about which image is better. This is evidenced by the fact that the patient frequently asks the technician to go back and forth several times between lenses before reluctantly making a decision. Of course, the optical technician has no way to "see" what the patient is actually seeing and has to rely on the patient's subjective memory skills and verbal communication.

Of current interest is a method and apparatus for objectively measuring the refractive properties of the eye, through direct observation of images, and without requiring an optical technician.

OBJECTS AND SUMMARY OF THE INVENTION

It is an object of the present invention to provide a method and apparatus for carrying out a self-administered exam for measuring eye refraction.

It is another object of the invention to provide such a method and apparatus for objectively measuring eye refraction and calculating diopter correction needed to correct eye refraction defects.

It is a further object of the invention to provide such a method and apparatus by which a person may make real time adjustment to viewed images until the "best" image is realized.

It is also an object of the invention to provide a patient interactive method and apparatus for measuring eye refraction.

It is also an object of the invention in accordance with one aspect thereof, to provide such a method and apparatus for measuring eye refraction along a number of axes to enable characterizing astigmatism.

The above objects and others not specifically recited are realized through a method and apparatus for measuring refraction of an eye in which the apparatus directs at least two (not necessarily simultaneously) spaced-apart narrow rays of light into the eye, with each ray traveling through a different portion of the eye's refractive elements. These rays of light simulate light traveling from a point source and are positioned and angularly oriented such that the rays impinge on the retina of the eye at a single point if the eye is properly refracting. If the eye is not properly refracting, the rays of light impinge on the retina at different locations.

When the rays of light impinge on the retina at different locations, the ray spacing and/or angular orientation are adjusted to cause impingement at a single point. The amount of adjustment required is then determined, and the necessary refractive correction calculated.

Additional objects and advantages of the invention will be set forth in the description which follows, and in part will be apparent from the description, or may be learned by the practice of the present invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE PREFERRED EMBODIMENTS

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the appended claims.

Figure 1:
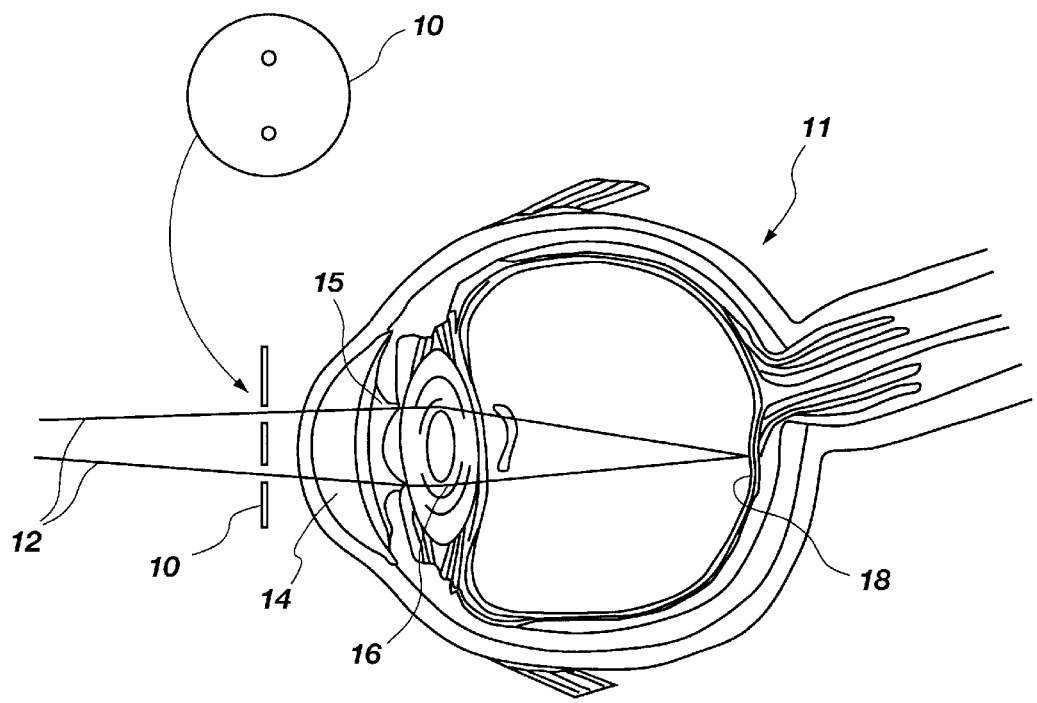
FIG. 1 is a side, cross-sectional view of an eye receiving light rays through a two pinhole disk and ultimately focusing on the retina at one location.

FIG. 1 is a side, cross-sectional view of an eye 11 receiving light rays 12 (originating from a point source not shown) through a two pinhole disk 10, shown in side view (and front view above the side view). The side view of the disk 10 shows light rays 12 traveling through the pinholes in the disk, through the aqueous humor 14 of the eye 11, through the iris opening (pupil) 15, and through lens 16 to meet and impinge at a single point on the retina 18 of the eye. The illustration of FIG. 1 is an example of an eye 11 properly refracting light rays 12 from a point source so that they focus on the retina 18 at a single point, and thus appear to the eye as a point source.

Figure 2:
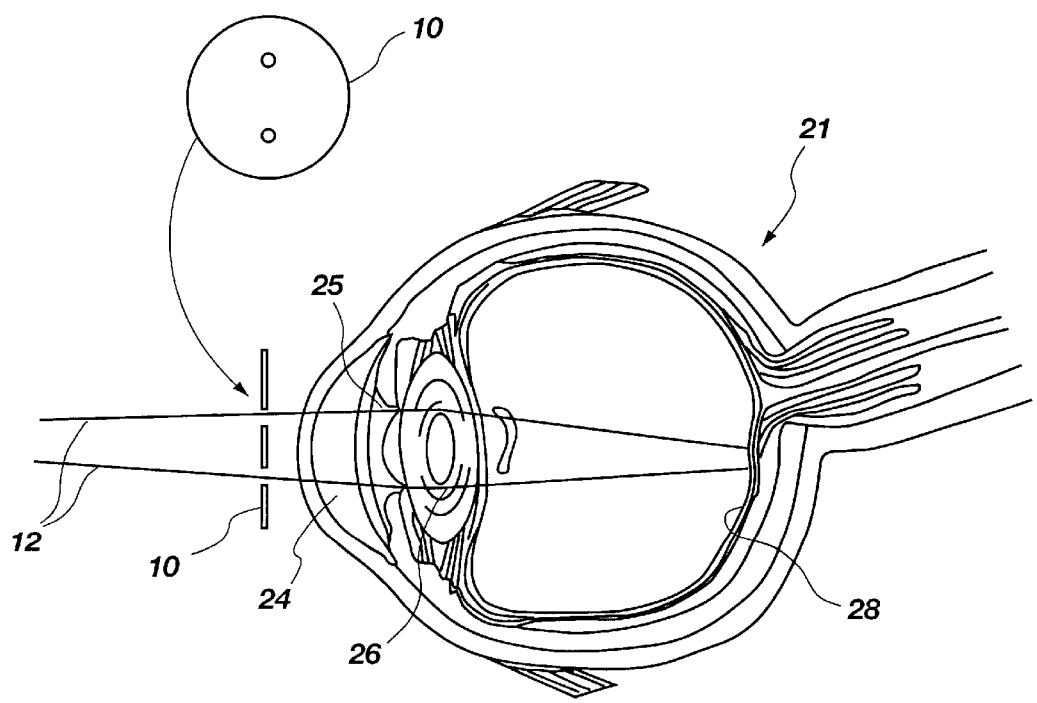
FIG. 2 is a side, cross-sectional view of an eye receiving light rays through a two pinhole disk and focusing on the retina at two spaced-apart locations.

FIG. 2 shows a side, cross-sectional view of an eye 21 which does not properly refract. The eye 21 is shown receiving light rays 12 (again originating from a point source not shown) through the two pinhole disk 10. The light rays 12 are shown traveling through the pinholes in the disk 10, through the aqueous humor 24, through the iris opening 25, and through lens 26 to impinge on the retina 28 at two different locations. In this example, the two light rays 12 are under-refracted so that the eye 21 does not focus on the point source of the light rays. Of course, over-refraction could also occur in which case, the light rays 12 would cross and impinge on the retina 28 at spaced-apart locations, again out of focus.

The purpose of a refraction exam is to determine the degree of external light bending or movement (by eyeglasses or other external lenses) of the light rays 12 necessary to cause the light rays to impinge on the retina at the same point. This, in effect, allows the eye to focus on the point source of the light rays 12.

Figure 2A:
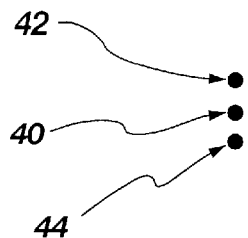
FIG. 2A illustrates the view of an improperly refracting eye when looking at a point source of light through a two pinhole disk.

FIG. 2A illustrates what an improperly refracting eye sees when viewing the point source(s) of light through the pinhole disk 10 (FIG. 2). That is, the eye sees two dots of light 42 and 44. On the other hand, a patient with an eye that properly refracts light sees a single dot 40. For the patient with the improperly refracting eye, the objective would be to determine the amount of bending of light rays required to cause dots 42 and 44 to move together and merge into dot 40, as the only dot seen.

Figure 3:
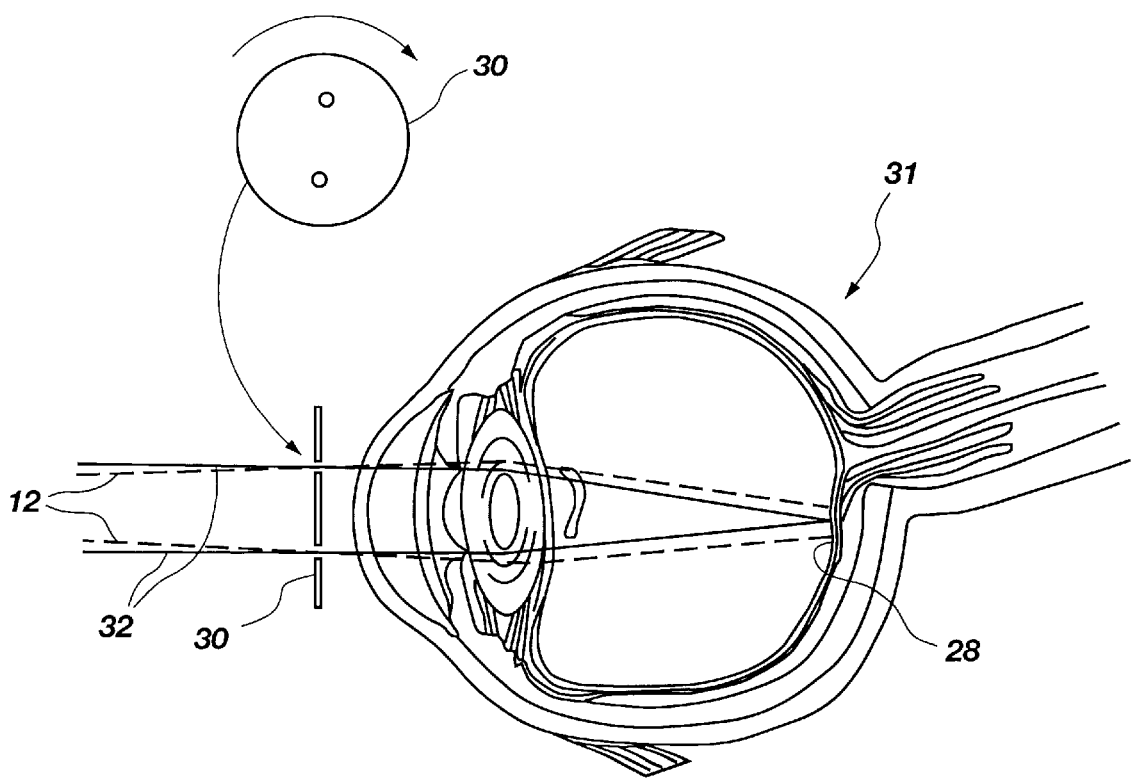
FIG. 3 is a side, cross-sectional view of an eye receiving light rays through a single pinhole disk that is rotated.

FIG. 3 shows how the bending or moving of incident light beams (by moving the light's point source location) can characterize (correct) improper refraction. Here, an eye 31 is receiving light rays 12 sequentially through a single pinhole disk 30 where the light rays originate from a light source or other display device such as a cathode ray tube, computer screen, etc. The disk 30 is rapidly rotated and the light ray source strobed so that the light is on and light rays are passed through the disk only when the pinhole is at the desired positions, in this embodiment, the upper and lower positions. For illustration, the side, cross-sectional view of the disk is shown to have two pinholes corresponding to the pinhole in the disk being rotated to its upper and lower positions. The light rays 12, shown in dotted lines, impinge on the retina 28 at two locations, just as in FIG. 2. In order for the light rays entering the eye 31 to come together at a single point on the retina, the light rays must be moved or bent to the position shown by (solid line) light rays 32. The amount of such movement or degree of such bending provides an indication of the eye refraction error and thus of the corrective lens needed to correct the error. Exemplary apparatus, by which light rays may be moved and the degree of movement measured for determining refraction error, are shown in FIG. 4.

Figure 4:
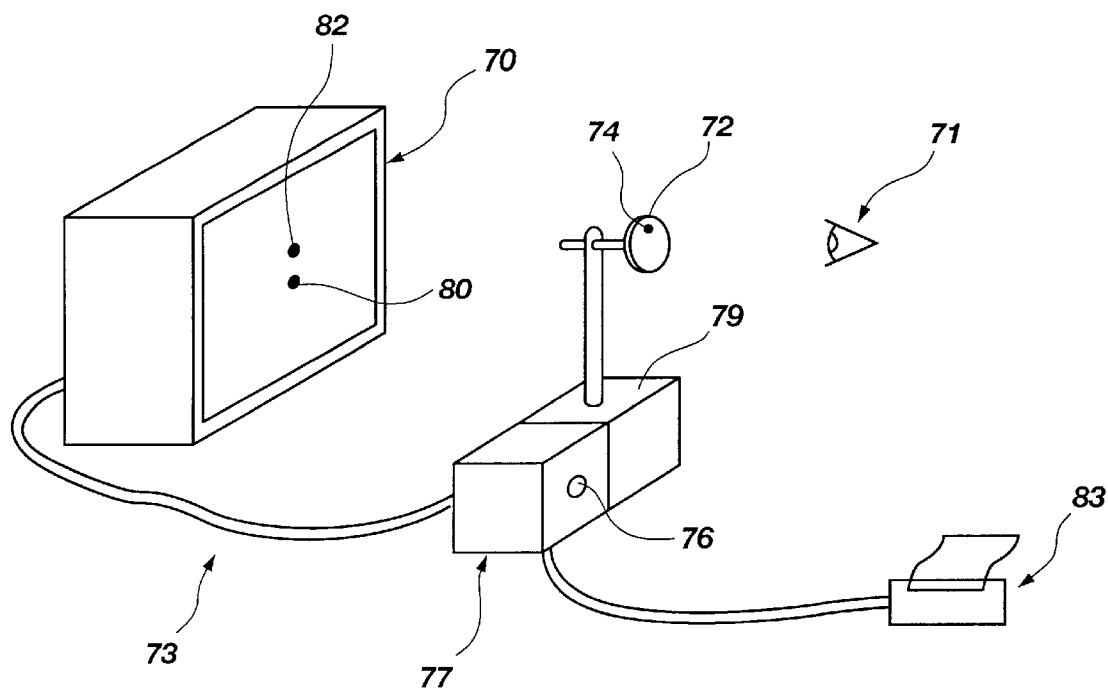
FIG. 4 shows a perspective view of patient-interactive apparatus made in accordance with the principles of the present invention, for measuring refraction of an eye.

FIG. 4 illustrates a patient-interactive apparatus 73 for measuring eye-refraction. The apparatus 73 includes a cathode ray tube (CRT) 70 (or other light source such as a video display) for emitting light forwardly from a first location 80 and a second location 82, spaced-apart vertically as shown. The apparatus 73 also includes a disk 72 disposed forwardly of the CRT 70 and including a single aperture 74. The aperture 74 selectively allows light emitted from the CRT 70 to reach the eye 71 of a patient. The disk 72 is mounted to rotate and the CRT 70 strobed such that light emitted from the first location 80 passes through the aperture 74 when it is at its lower position only. Likewise, the CRT 70 is strobed so that light emitted from the second location 82 passes through the aperture 74 only when it is at its upper position. Thus, the apparatus 73 simulates a stationary disk having both an upper aperture and a lower aperture for viewing a point source of light and provides for two rays of light to come through the pupil at different locations and with controllable ray directions. If the eye 71 properly refracts light rays, the eye will see a single point of light. Alternatively, if the eye 71 improperly refracts, the eye will see two points of light.

The disk 72 is mechanically coupled to a motor 79 that, in turn, is controlled by a microprocessor 77. The motor 79 causes rotation of the disk 72 under control of the microprocessor 77. When the disk 72 is rotated to the upper position and then to the lower position, etc., the microprocessor 77 signals the CRT 70 to emit strobe light from location 82 and then location 80, etc. In this manner, light from location 82 passes through the aperture 74 to the eye 71 when the aperture is in the upper position, and light from location 80 passes through the aperture to the eye when the aperture is in the lower position.

The microprocessor 77 includes a control knob or switch 76 by which a user may signal the microprocessor 77 to, in turn, signal the CRT 70 to alter the locations from which light is emitted from the display. Adjusting the knob 76 in one direction spaces the locations 80 and 82 farther apart while adjusting the knob in the other direction spaces the locations nearer to one another. By altering the spacing of the locations 80 and 82, the angle of the light rays from the CRT 70 to the aperture 74 and from the aperture to the eye 71 is altered. By altering these angles, the light rays entering the eye 71 can be made to impinge on the retina at the same point. Then, by measuring the degree of alteration, the refraction error, and thus the diopter correction necessary, can be determined.

Further, the microprocessor 77 can be programmed to measure the distance that the locations 80 and 82 are moved and from this measurement, to calculate the diopter correction necessary to cause the eye 71 to properly refract. With this approach, the required diopter correction may be objectively determined since the patient can precisely determine when the two light points are moved to become a single point. No back and forth comparison of images based on subjective memory is required, as is the case with the prior art.

Once the apparatus 73 determines the required diopter correction, the result is presented to the patient. This could be done by simply displaying the diopter correction required, on the CRT 70. Alternatively, the result could be printed by a printer 83. Those skilled in the art could easily identify other ways of presenting the results of the eye exam to the patient.

Alternatively to (or in addition to) moving the relative locations of the light spots 80 and 82 to alter the angles of the light rays, the radial location of the aperture 74 in the disk 72 could be changed instead. Changing the radial location could be done manually (stopping rotation of the disk 72 and moving the location of the aperture [to be discussed momentarily]) or automatically. Again, the amount of movement of the aperture 74 determines the degree of diopter correction necessary to correct any refraction error.

Figure 5:
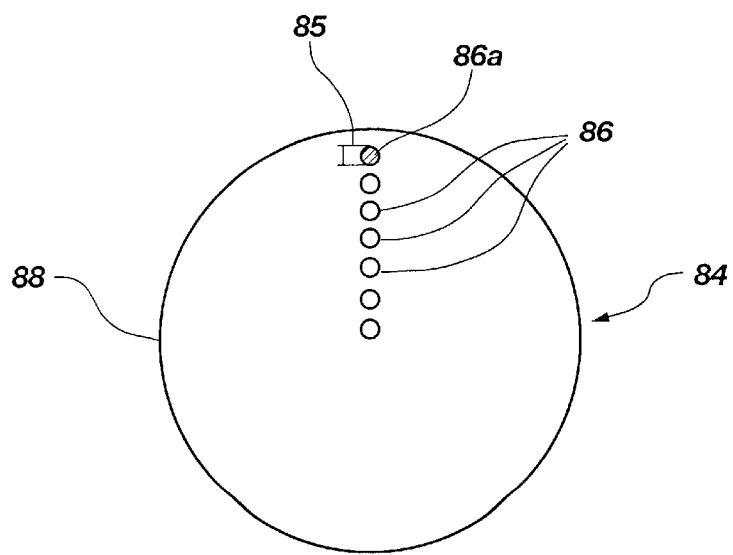
FIG. 5 shows a front view of a rotatable disk having a plurality of pinhole apertures, each aperture having a shutter mechanism.

FIG. 5 illustrates one embodiment of a disk 84 by which the radial position of an aperture may be varied. The disk 84 includes a plurality of pinhole apertures 86 disposed radially inwardly from the circumference 88 of the disk. (Twice the radial distance of the outermost aperture 86*a* must be equal to or less than diameter of the pupil of the eye being measured.) Disposed to selectively cover (or uncover) each pinhole aperture 86 is a shutter 85 in the form of a slidable plate attached so that it can be manually moved between positions covering or exposing said each pinhole aperture. Only one aperture on the disk 84 is exposed at a time.

In operation, a user will view the CRT 70 through the exposed aperture on the disk 84, as the disk is rotated and the light spots 80 and 82 are strobed, and if the user sees two dots, he/she stops the disk from rotating and slides the shutter plate to cover the exposed aperture and slides another shutter plate to uncover and expose a new aperture. This would be repeated until only one dot was viewed through the aperture of the rotating disk 84, indicating that the refraction error had been corrected.

Although FIG. 5 shows apertures 86 arranged linearly, other arrangements could also be provided. For example, the apertures could be spirally arranged, with adjacent apertures only slightly farther or closer to the center of the disk than the neighboring aperture. In this manner, very slight changes in the position of the aperture can be made. It is understood that when the aperture position is altered in the spiral arrangement, light from the CRT 70 would still be viewed only when the aperture were at the upper and lower positions of the disk, as previously discussed.

Figure 6:
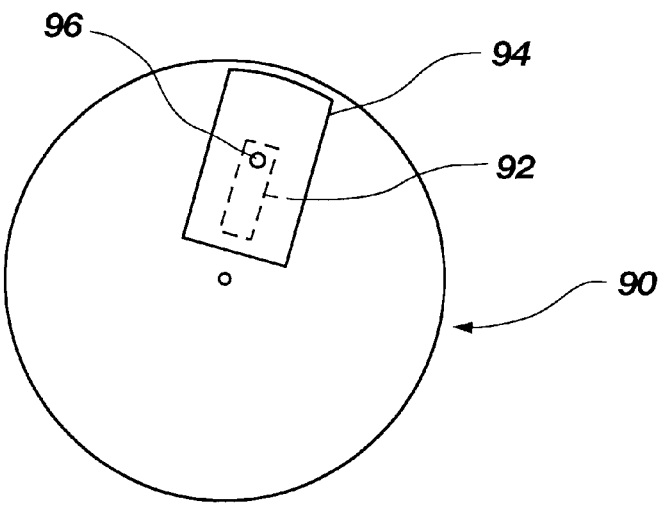
FIG. 6 shows a front view of a rotatable disk having a movable pinhole.

FIG. 6 shows another embodiment of a disk 90 which could be used with the apparatus of FIG. 4. This disk includes a radial slot 92, over which is disposed a radially slidable plate 94. The plate 94 includes an aperture 96. By moving the plate 94 radially inwardly or outwardly, the position of the aperture 96, and thus the angles of the light beams directed to the eye, can be changed.

Figure 7:
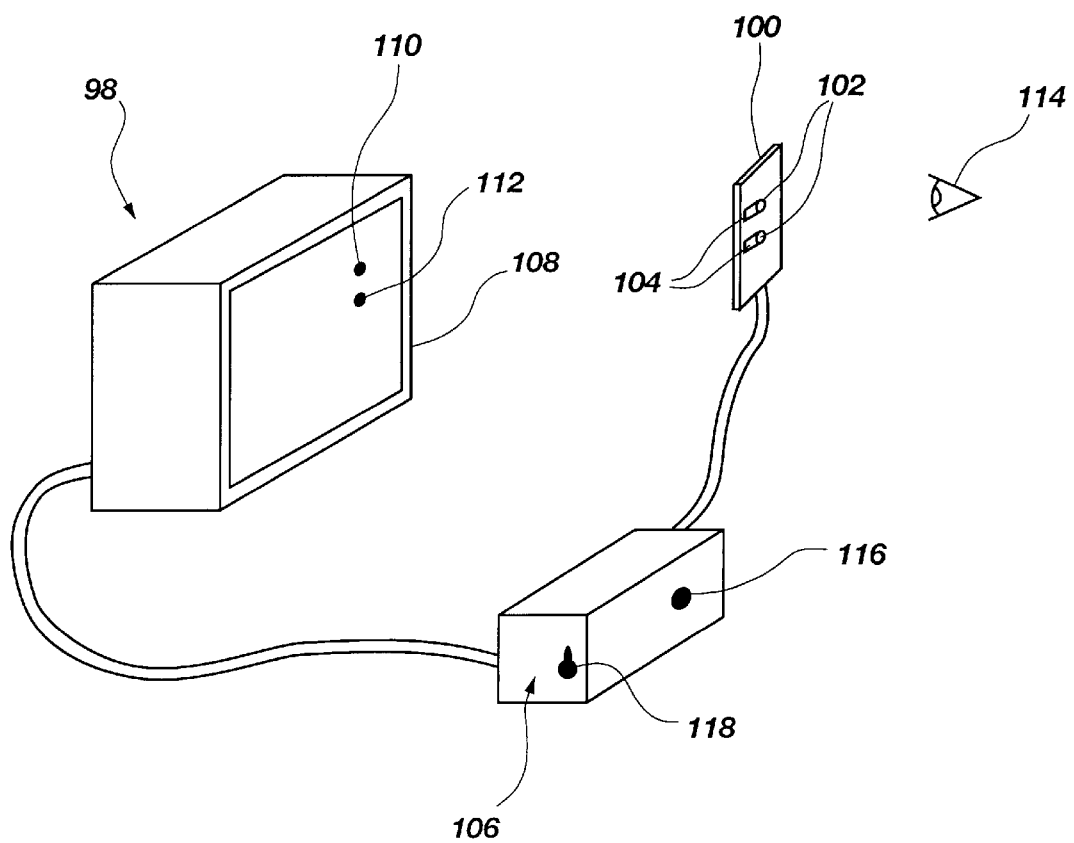
FIG. 7 shows a perspective view of another embodiment of patient-interactive apparatus made in accordance with the principles of the present invention, for measuring refraction of an eye.

FIG. 7 shows another embodiment of patient-interactive apparatus 98 for measuring eye refraction. This embodiment includes a shield 100 having at least two apertures 102 formed therein. Disposed to selectively cover each pinhole aperture 102 are shutters 104. The shutters 104 might be constructed in a variety of ways, including those already discussed. One such construction is an electronic integrated circuit shutter (e.g., LCD) controlled by signals from a microprocessor 106. The shutters 104 become opaque when a certain voltage or other control signal is applied thereto, and transparent when a different voltage is applied.

Like the FIG. 4 embodiment, a cathode ray tube display (or other light source) 108 emits light forwardly from a first location 110 and a second location 112. The microprocessor 106 is programmed to synchronize the opening of the upper aperture when the display 108 emits light from the first location 110, and alternately, to synchronize the opening of the lower aperture when light is emitted from the second location 112. Only one aperture is open at a time and only one display location emits light at a time. The microprocessor 106 controls the rapidly alternating opening of the apertures and emitting of light from the display locations.

Also similar to the FIG. 4 embodiment, a properly refracting eye 114 viewing the display 108 through the shield 100 sees a single point of light. If the eye 114 improperly refracts, the eye will see two points of light, but the user can adjust the locations from which light is emitted from the display 108 with a knob or switch 116 until the eye 114 only sees one point of light.

Figure 8:
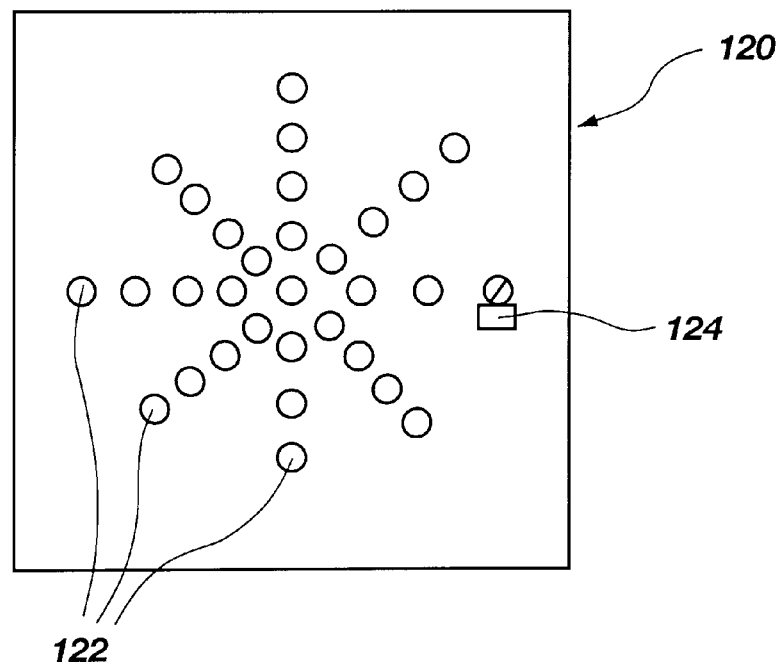
FIG. 8 shows a front view of a shield having multiple shuttered apertures.

Although the apertures 102 of FIG. 7 are shown being aligned vertically on the shield 100, other alignments could also be provided. FIG. 8 shows a shield 120 having apertures 122 disposed in multiple radial directions on the shield. Each aperture is shuttered as before discussed. With this shield, the pair of apertures employed to test eye refraction could be aligned vertically, horizontally, or diagonally as shown.

Whatever angle of alignment is used to test the refraction, the microprocessor 106 would signal the display 108 to emit light at locations complementary to the angle of the apertures. If vertical refraction is to be tested then the processor 106 must signal both the shield 120 and the display 108 so that upper and lower apertures alternate between open and closed conditions, while upper and lower display locations correspondingly alternate emitting light. Likewise, if horizontal refraction is to be tested, the processor would signal both the shield 120 and the display 108 so that left and right apertures alternate being opened and closed while left and right display locations correspondingly alternate emitting light.

With any of the apparatus described above, a patient can perform his/her own eye refraction exam. This is done by causing emission of light forwardly from first and second locations on a display. The light is selectively passed to the eye through pinhole apertures. As described above, light emitted from the first location passes through an aperture in a first position, and light emitted from the second location passes through an aperture in a second, spaced-apart position. If the patient sees two dots, he/she adjusts a control so as to move the dots together and form a single dot. The processor measures the distance the dots were moved and from this calculates the diopter correction required for the patient's eye.

The patient can repeat the process with the two dots aligned vertically, horizontally, or any other angle, and thus measure refraction error vertically, horizontally, etc. By measuring refraction vs. angle of alignment of the dots, astigmatism can be measured. This could be done by simply measuring refraction for one alignment, rotating or changing the angle of alignment, then measuring refraction again, etc. until the alignment has been rotated through 360°. When the exam is completed, the apparatus displays or prints out the results.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed and desired to be secured by United States Letters Patent is:

1. A patient-interactive apparatus for measuring refraction of an eye comprising means for selectively directing at least two spaced-apart narrow beams of light into the eye, said beams simulating light traveling from a point source and positioned and angularly oriented such that the beams would impinge on the retina of the eye at a single point if the eye were properly refracting but would impinge on the retina at two different points if the eye were not properly refracting, means for selectively adjusting the spacing and/or angular orientation between the beams of light to cause the beams to impinge on the retina of the eye at a single point, and means for determining the amount of adjustment made to the spacing and/or angular orientation between the light beams.

2. Apparatus as in claim 1 wherein said directing means comprises means for emitting light alternately from a first location and a second location, said first and second locations being spaced apart and said light being directed toward the eye, and aperture means disposed between the light-emitting means and the eye and defining a pinhole aperture, said aperture means being selectively moveable between a first position, at which time light from the first location is emitted, and a second position, at which time light from the second location is emitted.

3. Apparatus as in claim 2 wherein said light-emitting means comprises a video display means including a screen on which light is produced at the first and second locations, and wherein said adjusting means comprises control means coupled to the video display means for selectively causing the video display means to increase or decrease the spacing between the first and second locations.

4. Apparatus as in claim 3 wherein the first location is spaced approximately vertically above the second location, relative to the eye.

5. Apparatus as in claim 3 wherein the first location is spaced approximately horizontally apart from the second location, relative to the eye.

6. Apparatus as in claim 3 wherein the first location is spaced apart from the second location, at an angle between vertical and horizontal, relative to the eye.

7. Apparatus as in claim 2 wherein said aperture means comprises means for selectively varying the spacing between the first and second positions.

8. Apparatus as in claim 7 wherein said aperture means comprises a disk rotatable about a center axis, said disk including a pinhole aperture spaced radially from the center axis and rotatable successively to the first position, second position, first position, etc.

9. Apparatus as in claim 8 wherein said aperture means further comprises means for selectively moving the aperture closer or further away from the center axis.

10. Apparatus as in claim 1 wherein said directing means comprises a video display means responsive to electrical control signals for alternately producing first and second spaced-apart spots of light directed toward the eye, and shield means disposed between the video display means and the eye for selectively passing light from the first spot through a first location of the shield means to the eye, and from the second spot through a second location of the shield means to the eye, while blocking all other light from reaching the eye from the display means, and wherein said adjusting means comprises processor means, which includes manual manipulable input means, for transmitting electrical control signals to the video display to cause it to produce said first and second spots of light and to vary the distance therebetween as a result of manipulation of the input means.

11. Apparatus as in claim 10 wherein said determining means comprises processor means for calculating the amount of variation of distance between the first and second spots and the refraction error of the eye based upon the amount of variation of said distance.

12. A patient-interactive apparatus for measuring refraction of an eye, comprising:

means for emitting light forwardly from a first location and a second location, the second location being spaced laterally from the first location;

shield means disposed forwardly from the light emitting means for selectively blocking light from the light emitting means, and including first and second pinhole aperture means for selectively allowing light from the first location of the light emitting means to pass through the shielding means at the first aperture means to the eye, and light from the second location of the light emitting means to pass through the shielding means at the second aperture means, to the eye; and manual control means for selectively varying the angle of light traveling between the first location of the light emitting means and the first aperture means, and between the second location of the light emitting means and the second aperture means.

13. The patient-interactive apparatus of claim 12 wherein the shielding means comprises a disk rotatable about an axis and having at least one pinhole aperture therein.

14. The patient-interactive apparatus of claim 13 wherein the rotatable disk includes a plurality of pinhole apertures disposed at different distances outwardly of the axis, and a plurality of shuttering means, each for selectively shuttering a respective pinhole aperture.

15. The patient-interactive apparatus of claim 12 wherein the shielding means includes a plate having a plurality of pinhole apertures formed therein, and a plurality of shutter means for selectively opening or closing the plurality of pinhole apertures.

16. A patient-interactive method for measuring refraction of an eye comprising:

selectively directing at least two spaced-apart narrow beams of light into the eye, said beams simulating light traveling from a point source and positioned and angularly oriented such that the beams would impinge on the retina of the eye at a single point if the eye were properly refracting but would impinge on the retina at two different points if the eye were not properly refracting;

selectively adjusting the spacing and/or angular orientation between the beams of light to cause the beams of light to impinge on the retina of the eye at a single point; and determining the amount of adjustment made to the spacing and/or angular orientation between the light beams.

17. A method as in claim 16 wherein said adjusting step comprises adjusting the spacing between the beam of light, and wherein said determining step comprises determining the amount of adjustment made to the spacing between the light beams, and calculating the refraction of the eye from the amount of adjustment of the spacing.

18. A method as in claim 17 wherein said adjusting step further comprises successively adjusting the spacing generally horizontally, generally vertically, and at one or more angles between horizontal and vertical to cause the beam of light to impinge on the retina of the eye at a single point in each case, and wherein said determining step further comprises determining the amount of adjustment horizontally vertically, and at one or more angles between horizontal and vertical.

* * * * *